United States Patent
Liu et al.

(10) Patent No.: US 11,884,953 B2
(45) Date of Patent: Jan. 30, 2024

(54) METHOD FOR PREPARING PROTEIN PEPTIDE BASED ON CONNECTIVE TISSUE AND PREPARED PROTEIN PEPTIDE AND USE THEREOF

(71) Applicant: Shuang Liu, Jilin (CN)

(72) Inventors: Shuang Liu, Shuangliao (CN); Jinhao Liu, Shuangliao (CN); Jinhui Liu, Beijing (CN); Tiejun Gong, Shuangliao (CN); Wei Li, Shuangliao (CN); Yinshi Sun, Shuangliao (CN)

(73) Assignee: Shuang Liu, Shuangliao (CN)

( * ) Notice: Subject to any disclaimer, the term of this patent is extended or adjusted under 35 U.S.C. 154(b) by 651 days.

(21) Appl. No.: 16/755,854

(22) PCT Filed: Oct. 11, 2018

(86) PCT No.: PCT/CN2018/109924
§ 371 (c)(1),
(2) Date: Apr. 13, 2020

(87) PCT Pub. No.: WO2019/072219
PCT Pub. Date: Apr. 18, 2019

(65) Prior Publication Data
US 2021/0198713 A1    Jul. 1, 2021

(30) Foreign Application Priority Data
Oct. 11, 2017    (CN) .......................... 201710937035.1

(51) Int. Cl.
| | |
|---|---|
| C12P 21/06 | (2006.01) |
| A61K 9/19 | (2006.01) |
| A61K 35/28 | (2015.01) |
| A61K 35/32 | (2015.01) |
| A61K 35/34 | (2015.01) |
| A61K 35/36 | (2015.01) |
| A61K 35/38 | (2015.01) |

(52) U.S. Cl.
CPC ................ *C12P 21/06* (2013.01); *A61K 9/19* (2013.01); *A61K 35/28* (2013.01); *A61K 35/32* (2013.01); *A61K 35/34* (2013.01); *A61K 35/36* (2013.01); *A61K 35/38* (2013.01)

(58) Field of Classification Search
None
See application file for complete search history.

(56) References Cited

FOREIGN PATENT DOCUMENTS

| | | | |
|---|---|---|---|
| CN | 101851300 A | | 10/2010 |
| CN | 102357259 A | | 2/2012 |
| CN | 104164468 A | * | 11/2014 |
| CN | 104195205 A | | 12/2014 |
| CN | 106319009 A | * | 1/2017 |
| CN | 106699838 A | | 5/2017 |
| JP | S62-84025 A | | 4/1987 |

OTHER PUBLICATIONS

Estrella, Consuelo Amor S., et al. "Remodelling of the bovine placenta: Comprehensive morphological and histomorphological characterization at the late embryonic and early accelerated fetal growth stages." Placenta 55 (2017): 37-46 (Year: 2017).*
Banerjee, Pradipta, and C. Shanthi. "Isolation of novel bioactive regions from bovine Achilles tendon collagen having angiotensin I-converting enzyme-inhibitory properties." Process biochemistry 47.12 (2012): 2335-2346. (Year: 2012).*
Li et al., "Extraction and characterization of human-placenta collagen," Chinese Journal of Bioprocess Engineering, 2010, vol. 8, No. 3, pp. 58-61.
Jan. 17, 2019 International Search Report issued in International Patent Application No. PCT/CN2018/109924.

* cited by examiner

*Primary Examiner* — Robert J Yamasaki
(74) *Attorney, Agent, or Firm* — Oliff PLC

(57) ABSTRACT

A novel method for preparing an active protein peptide from connective tissue which includes steps of: connective tissue acquisition, segmenting, washing, pulverization, pH adjustment, enzymolysis, filteration, ultrafiltration, nanofiltration concentration, sterilization, freeze-drying, etc. The connective tissue protein peptide obtained by the method of the invention has features of high peptide content, high activity, etc., and the prepared active protein peptide of the connective tissue is easily absorbed by the human body, and has functions of preventing and/or alleviating and/or treating related diseases. Further, the method includes operation steps that are simple and easy to perform, which has low energy consumption, appropriate and effective utilization of animal natural resources, as well as environmental friendly, non pollution of environment, and low production costs, which is suitable for large-scale industrial production, and the purpose of efficiently preparing an protein active peptide from connective tissue can be achieved.

10 Claims, No Drawings

METHOD FOR PREPARING PROTEIN PEPTIDE BASED ON CONNECTIVE TISSUE AND PREPARED PROTEIN PEPTIDE AND USE THEREOF

PRIORITY

The present invention claims the priority of Chinese Patent Application (Application No. CN201710937035.1), entitled "Method for preparing protein peptide based on animal connective tissue and prepared protein peptide and use thereof", filed on Oct. 11, 2017, the entire contents of which are incorporated herein by reference.

TECHNICAL FIELD

The present invention relates to method for preparing protein peptide based on animal connective tissue and prepared protein peptide and use thereof, which belongs to the fields of physiological and biochemistry of meat protein, protein biochemistry and biological manufacture engineering technology etc.

BACKGROUND ART

In review of cytohistology, cell is the basic unit of livings. Tissues are constituted by cells having the same function, there are four types of tissues, which are neural tissue, muscle tissue, connective tissue and epithelial tissue, in which connective tissue is one of them. Connective tissue is one of the basic tissue of human and higher animals, consisting of cells, fibers and extracellular stroma. Cells include macrophages, fibroblasts, pulp cells, mast cells, etc. Fibers include collagen fibers, elastic fibers, and reticulated fibers, with the main function of connecting various tissues and organs. Matrix is a liquid with a slight adhesive viscosity, filled between cells and fibers, which functions as a medium for metabolic exchange of substances. Fibers and matrix together are referred as "interstitial", which is the largest component in connective tissue. Connective tissue has strong regeneration capacity, and healing of wounds is mainly accomplished by proliferation thereof. Connective tissue includes blood, lymph, loose connective tissue (e.g., subcutaneous tissue), dense connective tissue (e.g., tendon, sinew, bone marrow, periosteum, bone and cartilage), adipose tissue, etc. Connective tissue in vivo is widely distributed between cells, tissues and organs, and has a variety of functions such as ligation, supporting, nutrition, protection, etc. Intrinsic connective tissue, in turn, is divided into loose connective tissue, dense connective tissue, elastic tissue, adipose tissue and reticulated tissue. Loose connective tissue is also known as honeycomb tissue, characterized in that cells and the matrix thereof are relatively more, fiber content is less and distribution is loose. (1) fibers: include collagen fibers, elastic fibers and mesh fibers. ①collagen fiber: is also known as white fiber and is composed of collagen protein, with great toughness, strong tensile strength but poor elasticity. ②elastic fiber: is as known as yellow fiber, which composed of elastin protein with elasticity. ③mesh fiber: is distributed around capillary blood vessel. (2) matrix: matrix is a homogeneous substance without certain morphology, which has greater viscosity. (3) cells: include a plurality of different cells: fibroblasts cells, fiber cells, adipocyte, undifferentiated mesenchymal cells, macrophages cells, mast cells, which associated with allergic reactions, and white cells. The component of the dense connective tissue is basically the same as the loose connective tissue, wherein the collagen fibers are relatively thick, the quantity is large, the arrangement is tight, and mutually interweaved arranged, the type and number thereof are less, which mainly are fibroblasts and fiber cells. The dense connective tissue is distributed in the skin dermis, organ capsule, tendon, etc. 3. Elastic tissue is primarily distributed in arterial walls, ligaments, etc. 4. Adipose tissue is aggregated by a large number of adipose cells, and is separated by a small amount of loose connective tissue into a number of small leaves, which also divided into two types of yellow and brown. (1) yellow adipose tissue: distributed in subcutaneous, mesenteric, omentum, etc., presented in a shape of single bubble. It has functions of storing fat, keeping body temperature and providing heat energy; (2) brown adipose tissue: contains rich blood vessels and nerves, presented in a shape of multi-bubble, and distributed in the interaxillary region, axilla, etc., and the content is much higher in newborns, and the main function is generating a large amount of heat. 5. Mesh tissue is distributed in connective tissues of bone marrow, lymph nodes, spleen, lymphoid tissues, etc. The main components are proteins, the proteins include but not limited to antibodies, immunoglobulins, fibrin, collagen, elastin, cartilage mucin, glycoproteins, mucin, etc., and other chemical components include but not limited to hyaluronic acid, chondroitin sulfate, mucopolysaccharide, saccharide, lipid, etc.

In recent years, connective tissue diseases of connective tissues attract people's attention. The generalized connective tissue diseases also include a set of hereditary connective tissue diseases, i.e., diseases caused by abnormalities in the biosynthesis or degradation of certain components (e.g., collagen, elastin, or glycosaminoglycans) of connective tissue due to congenital defects. Connective tissue disease: a set of diseases with a pathological basis of loose connective tissue mucus-like edema and fibrin-like degeneration. It is believed that connective tissue disease primarily due to fibrin-like degeneration of collagen fibers, which therefor referred as diffuse collagen or collagen vascular disease, and later the disease considered not only limited to collagen fibers, which therefore renamed as connective tissue diseases. The etiology is not quite clear, and it is generally considered to have a certain relationship with genetic, immune and viral infection, etc., which is a multi-factor disease. With the progress of immunology, most connective tissue diseases are found to be accompanied by immunological abnormalities, such as low inhibitory T-cell function, hyperimmune function of body fluid, and some connective tissue diseases have self-antibodies, and thus the set of diseases also included in immunological diseases or autoimmune diseases. Connective tissue diseases include lupus erythematosus, scleroderma, dermatomyositis, rheumatoid arthritis, nodule polyarteritis, virginia granuloma, giant cell arteritis and drying syndrome, etc. According to the Rheumatism Classification of ACR (American College of Rheumatology), revised in 1982, the connective tissue disease may also include allergic vasculitis, belleville's disease, nodular non-suppurative heat-generating lipoidemia, etc. Connective connective tissue diseases have something in common, in the aspects of clinic, pathology and immunology, such as multi-system affliction (i.e., skin, joint, muscle, heart, kidney, hematopoietic system, central nervous system, etc.), long course of diseases, multiple changes, with fever, joint pain, vasculitis, increase of erythrocyte sedimentation rate, increase of gamma globulin level, etc., however, each has a characteristic performance.

Based on the knowledge of the inventors, there are many methods in the prior art with regard to the preparation of peptide processes from animal tissues. The common methods include water extraction method, acid extraction method, high-temperature low-pressure extraction method, drying method, alkali extraction method and enzymolysis extraction method. However, the active peptide provided by above methods is a denatured peptide. Therefore, the needs in the food, cosmetics, medicines and medicinal nutrition health-care products markets cannot be met, and a novel brand-new active peptide preparation method is urgently needed.

SUMMARY OF THE INVENTION

Based on the deficiencies of the prior art, the invention aims to provide a method for efficiently preparing freeze-dried powder of active protein peptide from connective tissue.

For achieving the purpose of the invention, the invention provides a method for preparing an active protein peptide from connective tissue, wherein the method comprises the following steps of: animal connective tissue acquisition, washing, shredding, pulp grinding or/and homogenizing, pH adjustment, enzymolysis, filtration, nanofiltration, degerming, vacuum ultra-low temperature freeze-drying, etc.

In another aspect of the present invention, a method of preparing an active protein peptide from connective tissue with steps of extraction and separation is provided, comprising steps of: connective tissue acquisition, segmenting, washing, pulverization, extraction, salting out, pulp grinding and/or homogenizing, pH adjustment, enzymolysis, ultrafiltration, nanofiltration concentration, sterilization, vacuum low temperature freeze-drying, etc.

In one aspect of the present invention, the method for preparing an active protein peptide freeze-dried powder from animal connective tissue comprises the following steps of: animal connective tissue acquisition, flushing, crushing, adding buffer solution to adjust pH to 6.5~8.0, pulp grinding and/or homogenizing, adding buffer solution to adjust pH to 6.5~8.0, enzymatic decomposition, centrifugal filtration, ultrafiltration desalination, nanofiltration concentration, and vacuum ultra-low temperature freeze-drying to prepare the active protein peptide freeze-dried powder. In one aspect of the present invention, the method for preparing an active protein peptide freeze-dried powder from animal connective tissue comprises the following steps of: animal connective tissue acquisition, flushing, crushing, adding buffer solution to adjust pH to 6.5~8.0, pulp grinding and/or homogenizing, adding buffer solution to adjust pH to 6.5~8.0, enzymatic decomposition, centrifugal filtration, ultrafiltration desalination, nanofiltration concentration, and vacuum ultra-low temperature freeze-drying to prepare the active protein peptide freeze-dried powder, wherein the specific steps are as follows:

1) animal connective tissue acquisition;
2) shredding;
3) after shredding, adding 5~10 times of volume of clear water or sodium bicarbonate solution or pH 6.5~8.5 buffer solution for stirring and washing;
4) extraction;
5) pulp grinding;
6) adjusting pH to 6.5~8.5, enzymolysis;
7) rough filtration;
8) filtering the filtrate by a filter membrane with molecular weight cut-off between 4500 and 10000, collecting the filtrate, then when adding the phosphate buffer solution to the original volume, repeatedly filtering for 3~5 times, and the residue is reserved for later use;
9) nanofiltration the filtrate by a nanofiltration membrane with molecular weight cut-off between 250 and 800 to concentrate the volume to $1/5$~$1/50$ of the original volume, then when adding the buffer solution to diluted the solution to the original volume, nanofiltration desalinating for 3~5 times;
10) degerming;
11) ultra-low temperature vacuum freeze-drying to prepare the connective tissue protein peptide freeze-dried powder.

In another aspect of the invention, a use of an active protein peptide prepared by the method of the present invention is provided, the use comprises the use of the active protein peptide for application of medicament for prevention and/or treatment of ageing of subject, food, health care product or cosmetic, suitably, the subject refers to mammal, preferably the subject refers to human.

In another aspect of the invention, the medicament, food, health care product or cosmetic is prepared as oral formulation, external formulation, inhalation formulation, nasal formulation, rectal formulation, transdermal formulation, or injection formulation, preferably as external formulation or injection formulation.

The advantage of the invention is the high activity and high purity of the prepared active protein peptide. The method is easy to operate and the production cost is low, which is suitable for large-scale industrial production, and the purpose of efficient preparation of active protein peptide from connective tissue can be achieved. The method is easy to operate and the production cost is low, which is suitable for large-scale industrial production, and the purpose of efficient preparation of protein peptide resources from connective tissue can be achieved. The filtrate obtained by centrifugation and filtration contain no harmful substances and cause no pollution to the environment.

EMBODIMENTS

In order to provide a substantial understanding of the invention, certain aspects, modes, embodiments, variations, and features of the invention are described in various details below.

In one embodiment of the present invention, a method of preparing an active protein peptide from connective tissue is provided, wherein the method comprises the specific steps of: animal connective tissue acquisition, washing, shredding, pulp grinding or/and homogenizing, pH adjustment, enzymolysis, filtration, nanofiltration, degerming, vacuum ultra-low temperature freeze-drying, etc.

The terms of the invention "animal" or "animal connective tissue" or "connective tissue" or "animal tissue" or "animal tissue organ" or "animal cell" or "animal body" or "part of animal body" or "primary preparation thereof" or "intermediate product thereof" or "final product", in some instances, has the same meaning, which may be used alternativly.

Animals used in the present invention include, but not limited to, all animals that may be derived from any kind of animal, including terrestrial or aquatic, including all the animals according to Genera of the family compendium classification of Kingdom, Phylum, Class, Order, Family, Genus, Species. For example, Protozoa, Mesozoa, Porifera, Placo~Zoa, Cnidaria, Ctenophora, Platyhelminthes, Nemertea, Gnathostomulida, Rotifera, Gastro~tricha, Kinorhyncha, Nematoda, Nematomorpha, Priapula, Acanthocephala, Entoprocta, Loricifera, Annelida, Echiura, Sipuncula, Pogonophora, Vestimentifera, Tardigrada, Onychopho~ra, Arthropoda, Mollusca, Brachiopoda, Ectoprocta, Phoronida, Chaetognatha, Echinoderma~ta, Hemichordata, and Chordata. The Chordata Phylum includes Urochordata, Cephochordata, Vertebrata. Wherein the Vertebrata includes Cyclostomata, Pisces, Amphibia, Reptilia, Ayes, Mammalia class, etc.

The animal may be derived from any kind of animal, which include terrestrial or aquatic, for example only, the land mammals herein include, but not limited to, man ape, chimpanzee, monkey, horse, cattle, bufflo, wild bufflo, pig, tiger, leopard, lion, lizard, hippo, sideburn dog, fox, hedgehog, snake, wild boar, sheep, donkey, deer, camel, alpaca, rat, kangaroos, elephant, horse, etc. The aquatic animals of the present invention include but not limited to crocodile, hippopotamus, giant salamander, turtle, seal, etc. Thus, the animals herein refers to all the animals capable of providing connective tissue, and the active protein peptide is prepared from the connective tissue.

The animal connective tissue is the connective tissues existing between various tissues, organs and cells, include but not limited to one or more connective tissues of carcass, skin, spine (e.g., cartialgenous), protuberance (e.g., hump, lion's milk), horn, head, brain, neck, ear, eye, nose, tongue, lip, oral cavity, esophagus, trachea, limbs, foot, toe, palm, bear's paw, claw, bone, cartilage, bone marrow, joint, membrane, ligament, tendon, tendon interval, sinew, tendon of beef and mutton, plate tendon, plate tendon tip, whole plate tendon, interrupted tendon, sinew tendon, spoon tendon, front tendon, rear tendon, tendon muscle, diaphragms, brisket tendon, sirloin tendon, strain tendon, muscle, skeletal muscle, smooth muscle, muscular septum, intestine, stomach, louver, tripe, blood vessel, aorta, heart, liver, kidney, offal, chest, lung, spleen, pancreas, egg, sperm, spermary, ovary, nerve, gallbladder, bladder, appendices, nerve fibers, blood, testis, penis (whip), calipash (water fish skirt), tail, etc., preferably one or more connective tissue present in skin, spine (e.g., cartialgenous), protuberance (e.g., hump, lion's milk), horn, tongue, esophagus, trachea, limb, foot, toe, bear's palm, claw, bone, cartilage, bone marrow, joint, membrane, ligament, tendon, tendon interval, sinew, tendon of beef and mutton, plate tendon, plate tendon tip, whole plate tendon, interrupted tendon, sinew tendon, spoon tendon, front tendon, rear tendon, tendon muscle, diaphragms, brisket tendon, sirloin tendon, strain tendon, muscle, skeletal muscle, smooth muscle, muscular septum, intestine, stomach, louver, tripe, blood vessel, egg, penis (whip), calipash (water fish skirt), tail, etc.; more preferably, one or more connective tissue present in spine (e.g., cartialgenous), protuberance (e.g., hump, lion's milk), horn, bone, cartilage, bone marrow, joint, membrane, ligament, tendon, tendon interval, sinew, tendon of beef and mutton, plate tendon, plate tendon tip, whole plate tendon, interrupted tendon, sinew tendon, spoon tendon, front tendon, rear tendon, tendon muscle, diaphragms, brisket tendon, sirloin tendon, strain tendon, smooth muscle, louver, tripe, etc.

In yet another embodiment of the present invention, the connective tissue is washed, which can be washed by a cleaning fluid of 1~10 times or more, and environment temperature can be controlled at any temperature from 0~25° C., preferably below 18° C., or below 16° C., even in a cold room with temperature of below 6° C. For the washing effect, those skilled in the art can make selections based on the actual observation of the state of the connective tissue. Washing may further remove floating fat and blood water from the connective tissues, typically more than 2 times, e.g., 3 times, 4 times, 5 times, etc. The cleaning fluid may be clear water or buffer, which may stabilize pH of the tissue or organ liquid. The buffer used may be any buffer with buffer range of pH 6.0~8.2. For example, MES (2 Morpholino Ethanesulfonic Acid) buffer, Bis~Tris buffer, HEPES buffer, PIPES buffer, MOPS buffer, Tricine buffer, TEA (triethanolamine) buffer, Glycine~Hydrochloric Acid buffer, Phthalic Acid-Hydrochloric Acid buffer, Disodium hydrogen phosphate~citric acid buffer, Citric acid~sodium hydroxide~hydrochloric acid buffer, Citric acid~sodium citrate buffer, Acetic acid~sodium acetate buffer, Potassium hydrogen phthalate~sodium hydroxide buffer, Carbonate buffer, Disodium hydrogen phosphate~sodium dihydrogen phosphate buffer, Disodium hydrogen phosphate~potassium dihydrogen phosphate buffer, Potassium dihydrogen phosphate~sodium hydroxide buffer, barbital sodium-hydrochloric acid buffer, Tris~HCl buffer, and any saline solution that can be adjusted. In one embodiment of the invention, the buffer used is phosphate buffer having concentration of 1~50 mM phosphate buffer, e.g., 5~40 mM, 5~30 mM, 5~25 mM, 10~25 mM, 10~20 mM. Suitably contains 0.1 M~2 M NaCl, e.g., 0.01 M~2 M, 0.01 M~1.5 M, 0.01 M~1 M, 0.01 M~0.5 M, 0.01 M~0.3 M.

In one particular aspect of the present invention, the buffer is a pH 6.5-7.8 phosphate buffer containing 50 mM~0.5 M NaCl, 1~20 mM phosphate.

The connective tissue used in the present invention may be fresh, fresh refrigerated, quick-frozen or frozen, rough finished, fine finished, dried or salted, preferably fresh, fresh refrigerated, quick-frozen or frozen; more preferably, fresh or fresh refrigerated or quick-frozen; most preferably, fresh.

The term "fresh" refers to immediate removal of animal's target organ or tissue after slaughtering the live animal, and directly for experiment use, the shorter the time from slaughter to experiment, the better. The materials used include various animals that are purely natural organic and nuisance-free, for example only, include but not limited to mammal, poultry, fish, etc. In particular, a majority of consumer-favorite animal edible parts. In the low-temperature production environment, the tissue organ repair agent of various fully-active animal protein peptide super-vacuum low-temperature freeze-dried powder is manufactured by utilizing the high-novel technology and the advanced technology step of keeping the total activity of the protein. The 3D full information active protein peptide freeze-dried powder produced by the company adopts core technology of autonomous research and development, and protein biochemical engineering and other sophisticated process of maintaining protein and the peptide fully active are adopted, during various production steps of preparation of protein active peptide crystallization freeze-dried powder, from material selection to step of vacuum ultra-low temperature freeze-drying, and the produced product maintain a protein three-Dimensional structure, the original biological activity of the protein peptide is retained, which allow the function of the protein peptide not to be destroyed and lost due to the manufacturing process, and meanwhile, the effect of direct absorption of the mucosa is achieved. Repair and rehabilitation of human tissue organs from full biological information is achieved. The "animal whole-active protein peptide vacuum ultra-low temperature freeze-dried powder" series of products contain a plurality of functional substances, such as immune enhancement factors, hematopoietic factors, regeneration factors, superoxide dismutase, repair polypeptides, 29 type collagen, elastin, cellular signal mediating proteins, and other various active proteins or enzymes, etc., which are the indispensable factors for the growth, development and repair of cells, tissues or organs. Extraction of animal protein peptide essence via an ultra-low temperature freeze-drying technology, can effectively improve the absorption of animal protein peptide by human bodies, and the purpose of preventing and/or alleviating and/or treating and/or curing pathological symptoms or diseases caused by human tissue organ deletion and recession is achieved. The series of products can prevent and/or alleviate and/or treat and/or cure pathological symptoms or diseases caused by deletion and recession of human tissue organs, which include, but not limited to, one or more clinic pathological symptoms or diseases of groups consisting of, ageing and wrinkled skin, abnormal increase of freckles and crow's feet, arthritis, rheumatoid, rheumatoid spondylitis, intervertebral disc injury, osteoporosis, cardiovascular disease, sub-health or secondary-health, myocarditis, hyperlipemia, hypertension, hyperglycemic, lipid deposition caused by metabolic disorders, obesity, arteriosclerosis, prostatitis, respiratory infectious diseases, senile dementia, fatigue, insomnia, amnesia, anorexia, fidgety, depression or negativity, anxiety, dizziness, aging, palpitation, abnormal defecation, low sexual desire, decreased immune function (common cold or cold symptoms, throat discomfort, oral ulcer, etc.), diabetes, ageing disease, coronary heart disease, sexual dysfunction, chronic obstructive emphysema, hepatitis, fatigue, neurasthenia, cerebral infarction, asthma, cough, adult respiratory distress syndrome, etc.

As used in the specification and the appended claims, the singular forms "a", "an" and "the" include plural referents unless the content clearly dictates otherwise. For example, reference of "an animal panel tendon(fascia)" includes a single mammalian fetus and its animal panel tendon(fascia), a combination of two different mammalian fetus and its animal panel tendon(fascia) or more mammalian fetus and their animal panel tendon(fascia), etc.

In yet another embodiment of the present invention, the animal fetus and its animal panel tendon(fascia) are cut into slices, blocks, filaments, strips, chopped into a powder shape and/or mechanically pulverized into slurry, preferably in the form of powder or slurry, which allow the shape more conducive to the extraction step as follows.

The term "low temperature maintain" includes both "refrigeration maintain" and "cryopreservation."

In another embodiment, refrigeration maintain refers to incubate mammalian fetus and animal's panel tendons at temperature of below about 10° C., for example, between above 0° C. and about 9° C., suitably between about 1° C. and about 8° C., suitably between about 2° C. and about 6° C., preferably between about 2° C. and about 4° C.

In one embodiment, the mammalian fetus and its animal panel tendons can be refrigerated for tens of minutes to 7 days, or even longer. Sometimes for production purposes, if the ambient temperature is relatively low, even specialized refrigeration maintaining equipment is not utilized. For example, in autumn time in northeast, when the temperature is relatively low. If refrigeration is required, sometimes refrigeration time only required for tens of minutes, hours, or 1 day, 2 days, 3 days, 4 days, 5 days, 6 days, 7 days. However, considering factors such as microbial spoilage and odor, usually no more than 7 days.

In another embodiment, the mammalian fetus and its animal panel tendons can be cryopreserved at a temperature below about 0° C., such as between below 0° C. and about −180° C. (e.g., liquid nitrogen), suitably between about −20° C. and about −180° C. Considering numerous factors such as power consumption and raw material operation costs, it is suitable to freeze the deposit between about −25° C. to about −80° C., preferably between about −25° C. to about −40° C.

In one embodiment, the mammalian fetus and its animal panel tendons may be cryopreserved for about 1 day to 35 days or even longer, suitable cryopreserved for between about 2 days and 20 days, preferably between about 5 days and 10 days.

In another embodiment, the meat may be cryopreserved with the composition at temperature below about −0° C., for example, between about 0° C. and about −180° C. (e.g., liquid nitrogen), suitably between about −20° C. and about −80° C., suitably between about −25° C. and about −80° C., suitably between about −25° C. and about −80° C., preferably between about −25° C. and about −40° C.

In yet another embodiment of the present invention, the powder or slurry particles is pulverized. The term "pulp grinding" refers to performing a fine chemical process by mechanically pulverizing connective tissue particles in a liquid, i.e., homogenizing or pulp grinding. The fineness of the pulped particles can sometimes be up to less than 500 mesh.

In some embodiments of the present invention, the protein slurry is extracted, and the extraction is an acid extraction selected from groups consisting of citric acid, malic acid, hydrochloric acid, boric acid, nitric acid or (glacial) acetic acid for protein extraction. Preferably citric acid, malic acid, glacial acetic acid; most preferably, glacial acetic acid.

By volume ratio, the volume ratio of connective tissue to liquid acid used for extraction (vol:vol) is 1:1~100; preferably 1:1~50; More preferably, 1:1~20, most preferably 1:1~5. The concentration of acid depends on the nature of the particular acid, in the case of using acetic acid, the final concentration may be 0.01%~99.5, such as 0.01%~15%, 0.01%~10%, 0.01%~5%, 0.05%~15%, 0.05%~10%, 0.05%~5%, 0.05%~3%, 0.05%~1%, such as 0.1, 0.2, 0.3, 0.4 or 0.5%.

The pH of the above extraction ranges from 1 to 6.8, such as pH is 6.8, 6.7, 6.6, 6.5, 6.4, 6.2, 6.1, 6.0, 5.9, 5.8, 5.7, 5.6, 5.5, 5.4, 5.3, 5.2, 5.1, sometimes even below 5 is possible, for example pH below 4.5, 4.0, 3.5, 3.0, even below 2.0, e.g., below 1.0.

The temperature of the extraction can be selected to be carried out at room temperature, or below room temperature, below 20° C., e.g., below 10° C., below 6° C. below 4° C., or near 0° C.

The extraction time is determined according to the extraction temperature, the extraction effect and the nature of the active protein peptide, for example within 7 days, and the extraction within 1 day, 2 days, 3 days, 4 days, 5 days and 6 days. For example, extraction for 1~7 days, 1~6 days, 1~5 days, 1~4 days, 1~3 days, 1~2 days, and in some embodiments, the extraction time is controlled within 24 hours, e.g., 0.5~24 hours, 1~20 hours, 2~16 hours. Those skilled in the art will select a appropriate extraction time based on the concentration and effect of the extraction liquid.

The temperature condition for the entire embodiment may be controlled at 1~18° C., e.g., 1~16° C., 1~14° C., 1~10° C., preferably below 8° C., more preferably below 6° C., and most preferably below 4° C.

In yet another embodiment of the present invention, an active protein peptide is provided, wherein the percentage of ACE (angiotensin converting enzyme) inhibition and $IC_{50}$ are both used for representation. When the percentage of ACE (angiotensin converting enzyme) inhibition is used as the viability parameter, the ACE effect of the peptide obtained by the various preparation methods was first compared. In some embodiments of the invention, when the protein concentration is 1.0 mg/mL, the active protein peptide has an ACE inhibitory rate of more than 10% and an $IC_{50}$ of less than 2.0 mg/mL; when the protein concentration is 0.5 mg/mL, the active protein peptide has an ACE inhibitory rate of more than 15% and $IC_{50}$ of less than 1.0 mg/mL; when the protein concentration is 0.1 mg/mL, the active protein peptide has an ACE inhibitory rate of more than 20% and an $IC_{50}$ of less than 0.5 mg/mL; when the protein concentration is 0.05 mg/mL, the active protein peptide has an ACE inhibitory rate of over 30% and an $IC_{50}$ of less than 0.1 mg/mL. Further, more than 10% of ACE is inhibited, e.g., more than 20%, 30%, more than 35%, even more than 40% of ACE is inhibited when using a protein peptide production prepared according to the present invention at a concentration of 0.01 mg/mL. $IC_{50}$ is an indicator for measuring the effect of ACE inhibitors, and it is also an indicator of the activity of the protein. The $IC_{50}$ of the various proteins prepared using the method of the present invention is less than 1.0 mg/mL, e.g., less than 0.9 mg/mL, 0.8 mg/mL, 0.7 mg/mL, 0.6 mg/mL, 0.4 mg/mL, 0.2 mg/mL, 0.1 mg/mL, 0.08 mg/mL, 0.06 mg/mL, 0.05 mg/mL, 0.04 mg/mL, 0.03 mg/mL, 0.02 mg/mL, 0.01 mg/mL, all possible.

As used in this specification and the appended claims, the singular forms "a", "an" and "the" include plural referents unless the content clearly dictates otherwise. For example, said "an animal panel tendons" includes a single mammalian fetus and its animal panel tendon, a combination of two different mammalian fetus and its animal panel tendons or more mammalian fetus and their animal panel tendons, etc.

In yet another embodiment of the present invention, a low temperature maintaine method of a mammalian fetus and its animal panel tendon is provided. The fetus and the animal plate tendon thereof can be stored in a whole block, also can be stored in a plurality of large blocks or even pulverized. The invention can directly use the fresh fetus and its animal plate tendon tissue, and can also use the low-temperature maintained fetus and its animal plate tendon tissue.

External pollution: food contaminated by microorganisms other than the raw materials and semi-finished products in the processing process, such as bacterial contamination in water, secondary pollution of bacteria in the air, secondary cross infection of staff hands, equipment, containers, tools, turnover boxes, etc., and the polluted packaging materials, etc. Degerming of water is generally performed by ultraviolet disinfection, ozone disinfection; bacteria killing in air: plasma diffusion technology, food dynamic disinfection machine or air purification system; hand bacteria disinfection: blow-drying by hot air, after washing hands with a lotion, adding 75% acetic acid into the automatic induction hand sanitizer, and the disinfection liquid automatically is sprayed out to disinfect the hands, which allow the disinfectant directly enter the workshop.

Internal pollution: bacteria contained in raw materials and semi-finished products. It can be divided into baking, beverage, aquatic products, leisure food, convenience food, beer, bean products, nutrition products, etc., which need different sterilization equipment and technology.

In some embodiments of the present invention, the plant or equipment used to produce the product are sterilized, the equipment include, but not limited to, ultraviolet sterilization, ozone disinfection, disinfection treatment of the product or intermediate product, include, but not limited to, microwave sterilization, gene sterilization, electron-ray sterilization, magnetic sterilization, resistance heating sterilization, pasteurization, ultra-high temperature transient sterilization (UHT), overheat steam sterilization technology, irradiation sterilization technology, ultrahigh pressure sterilization technology, ultrasonic sterilization technology, and sterilization technology. Preferably, the sterilization means and methods do not destroy the activity or spatial structure of the protein, such as ultra-high pressure sterilization technology.

In one embodiment of the present invention, The enzyme is selected from one or more combinations of groups consisting of serine protease, alkaline protease, sulfhydryl protease, neutral protease, bromelain, metalloproteinase, aspartic protease, carboxypeptidase, pepsin, chymotrypsin, trypsin, cathepsin K, chymotrypsin, flavor protease, compound protease, papain, and subtilisin. Preferably, one or more combinations of enzymes consisting of serine protease, alkaline protease, neutral protease, pepsin, trypsin, compound protease, and papain; more preferably, one or more combinations of groups consisting of neutral protease, pepsin, trypsin and papain; more preferably a combination of one or two of groups consisting of pepsin, trypsin, and papain; most preferably the enzyme used for enzymolysis is pepsin or trypsin or papain.

In the process of enzymolysis, the temperature of the connective tissue slurry is adjusted to 0~65° C., and the time of enzymolysis is 0.5~48 hours. For example, in the enzymolysis process, first step is to adjust the temperature of connective tissue slurry to 0~55° C., and the time of enzymolysis is 2~48 hours; or in the enzymolysis process, first step is to adjust the temperature of connective tissue slurry to 0~45° C., and the time of enzymolysis is 2~36 hours. In the enzymolysis process, first step is to adjust the temperature of connective tissue slurry to 15~45° C., and the time of enzymolysis is 4~24 hours. In the process of enzymolysis, first step is to adjust the temperature of connective tissue slurry to 30~45° C., and the time of enzymolysis is 8~24 hours. Another embodiment of the present invention is the use of centrifugal operation to the extracted sample, which may employ a variety of centrifugal equipment commonly used in the laboratory, such as a vacuum centrifuge, or a non-vacuum centrifuge. The centrifugal equipment can be divided into low-speed, high-speed and over-speed centrifuges according to the rotating speed. The centrifugal equipment can be divided into a freezing centrifuge or a normal-temperature centrifuge according to whether the refrigeration is carried out or not. Industrial production commonly used centrifuge, such as a high-speed continuous centrifuge. Typically, the centrifugal force is set in units of G to calculate the speed, the centrifugal force can be above 100,000 g, and also can be between 1000 g and 20,000 g, such as between 1000 g and 10000 g, preferably 8000 g, more preferably 100,000 g. Centrifugation can also be expressed in RPM, for example, above 1000, 1500, 2000, 3000, 5000, 10000 rpm, above 15000 rpm, 20000 rpm or even above 100000 rpm. The centrifugation temperature may be carried out at room temperature or below room temperature, for example, below 20° C. or 15° C., preferably below 10° C., more preferably is 6° C., or below 4° C. Centrifugation time can be any time, while centrifugation time should not be too long which may lead to excessive impurities precipitation and thereby cause reduced harvest, and too long time can also easily lead to collagen degeneration. Usually within 1 hour, such as 40 minutes, 30 minutes, or 20 minutes. After centrifugation, the supernatant containing impurities can be effectively removed, and the precipitated crude product containing the active protein peptide is retained.

The pH of precipitated crude product of the active protein peptide can be adjusted, the pH range is acidulous, neutral or alkalescence, and suitably is neutral or alkalescence. For example, pH 6~9, preferably 6.5~8.0, more preferably 6.8~7.8, and most preferably 7.0~7.5, such as 7.0, 7.1, 7.2, 7.3, 7.4, 7.5.

In yet another embodiment of the present invention, a method of filtering and nanofiltration desalination of high-activity protein or protein peptide crude product is provided, filtering process is conducted by a plate basket filter press and a gauze filter. The commonly used plate basket filter press is manual plate frame filter press, mechanical plate frame filter press, and hydraulic plate frame filter press, typically filters equipped with a filter membrane, and the membrane size can be arbitrarily adjusted, for example, 5 μm, 2 μm, 1 μm, 0.45 μm, 0.2 μm, 0.1 μm, 0.05 μm, etc. Meanwhile, concentration desalination is carried out by nanofiltration machine, and commonly used nanofiltration machine is hollow fiber column type nanofiltration machine and reverse osmosis nanofiltration machine. The filtration membrane or nanofiltration membrane has no strict distinguishing boundary, usually the molecular weight of between 1000 and 100,000 is filter membrane, and molecular weight of between 50 and 1000 is nanofiltration membrane. The filter typically has a filter membrane which is sized according to the size of the trapped protein molecule, typically having a molecular weight between 1000-100,000, such as between 1000-50,000, between 1000-30,000, between 1000-20,000, between 1000-15,000, between 1000-10,000, between 1000-8000, between 1000-6000, between 1000-5000, between 1000-3000, etc. The nanofiltration machine typically has a nanofiltration membrane which is sized according to the size of the trapped protein molecule, typically having a molecular weight between 50 and 1000, between 50-800, between 50-600, between 100-600, between 200-600, between 200-500, between 200-400, etc.

The purpose of the invention is to provide a specific method for efficiently preparing an active protein peptide freeze-dried powder from connective tissue and connective tissue thereof, which is also low cost.

In one aspect of the present invention, the method for preparing active protein peptide freeze-dried powder from animal connective tissue comprises the following steps: animal connective tissue acquisition, flushing, crushing, adding clean water, extraction, salting out, pulp grinding and/or homogenizing, adding buffer solution to adjust pH to 6.5~8.0, enzymolysis, centrifugal filtration, ultrafiltration desalination, nanofiltration concentration, and vacuum ultra-low temperature freeze-drying to prepare the active protein peptide freeze-dried powder.

In one aspect of the present invention, the method for preparing active protein peptide freeze-dried powder from animal connective tissue comprises the following steps: animal connective tissue acquisition, flushing, crushing, adding clear water, extraction, salting out, pulp grinding and/or homogenizing, adding buffer solution to adjust pH to 6.5~8.0, enzymolysis, centrifugal filtration, ultrafiltration desalination, nanofiltration concentration, and vacuum ultra-low temperature freeze-drying to prepare the active protein peptide freeze-dried powder, wherein the specific steps are as follows:

1) animal connective tissue acquisition;
2) shredding;
3) after shredding, adding 5~10 times of volume of clear water for stirring and washing;
4) extraction;
5) salting out;
5) pulp grinding and/or homogenizing;
6) adjusting pH to 6.5~8.5, enzymolysis;
7) rough filtration;
8) first filtering the rough filtrate by a filter membrane with molecular weight cut-off between 4500~10000, collecting the filtrate, then when adding the phosphate buffer solution to the original volume, repeatedly filtering for 3~5 times, and preserving the residue for later use;
9) nanofiltration the filtrate by a nanofiltration membrane with molecular weight cut-off between 250 and 800 to concentrate the volume to ⅕~1/50 of the original volume, then nanofiltration desalinating for 3~5 times when adding the phosphate buffer solution to diluted the filtrate to the original volume;
10) degerming;
11) ultra-low temperature vacuum freeze-drying to prepare the connective tissue protein peptide freeze-dried powder.

In another embodiment of the present invention, a use of the active protein peptide production made by the method of the present invention is provided, the use comprise the use of said active protein peptide for application of medicament for prevention and/or control ageing of subject, food, health care product, or cosmetic product.

In yet another embodiment of the present invention, the medicament, food, health care product or cosmetic is prepared as oral formulation, external formulation, inhalation formulation, nasal formulation, rectal formulation, transdermal formulation, or injection formulation, preferably external formulation or an injection formulation.

In yet another embodiment of the present invention, a prophylactic and/or therapeutically effective amount of active peptide prepared according to the present invention may be administered to a person daily, which may be any effective amount, such as 0.5 ug/kg, 1 ug/kg, or 10 ug/kg of human body weight, and suitably effective amount include administering to human the active peptide from about 1 ug/kg to about 10,000 mg/kg body weight per day.

The invention can be better understood by the following examples, but should not limited to these examples.

EXAMPLES

Example 1

Preparation of Bone Active Peptide Freeze-Dried Powder from Animal Bone

Animal hard bones include, but not limited to, pig bones, cattle bones, sheep bones, horse bones, fish bones, etc. Depending on the part, it is possible to take the animal bone, cull the surrounding connective tissue, and the attached tissue of the tendon. An alternative technology is to remove bone marrow present in the central portion of the bone tissue.

1) slaughtered cattle bone was taken, and crushed, to prepare bone powder;
2) 10 Kg of the bone powder was taken, and extracted by 5~10 times volume of 0.05 MNaCl~3 MNaCl phosphate buffer solution (pH 6.0~8.0);
3) filtered to remove residue and collected the supernatant to obtain a crude protein product;
4) 2% trypsin or 2.5% papain was added for enzymolysis;
5) the crude protein peptide product was filtered with 0.2 μm filter membrane;
6) firstly the crude filtrate was filtered by a filter membrane with molecular weight cut-off between 4500~10000, and the filtrate was collected, then when the phosphate buffer solution was added to the original volume, repeatedly filtered for 3-5 times, and the residue was preserved for later use;
7) nanofiltration of the filtrate was carried out by a nanofiltration membrane with molecular weight cut-off between 400-500 to concentrate the volume to ⅒~1/50 of the original volume; then nanofiltration desalinated for 3~5 times when the phosphate buffer solution was added to dilute the buffer solution to the original volume;
8) degerming and filteraration, freeze-drying was carried out to prepare the bovine connective tissue protein peptide freeze-dried powder.

Example 2

Preparation of an Active Peptide Freeze-Dried Powder from Cattle Bone 1) slaughtered cattle marrow bone was taken, and crushed, to prepare bone power;
2) 5~10 times of the volume of deionized water was added into the above bone powder for grinding;
3) 10 Kg of the bone powder was taken, and extracted by acetic acid with final concentration of 0.05~25% for 4~24 hours;
4) filtered to remove residue and collected the supernatant to obtain a crude protein product;
5) 3~5 weight volume of phosphate buffer solution was added to the protein crude product for stirring, pH was adjusted to 6.8~7.4, which contains 0.05 M~0.1 M NaCl;
6) 1-3% 0 of pepsin was added for enzymolysis;
7) the protein peptide crude product was filtered with 0.2 μm filter membrane;
8) firstly the crude filtrate was filtered by a filter membrane with molecular weight cut-off of 8000, and the filtrate was collected, then when the phosphate buffer solution was added to the original volume, repeatedly filtered for 3-5 times, and the residue was preserved for later use;
9) nanofiltration of the filtrate was carried out by a nanofiltration membrane with molecular weight cut-off between 600 to concentrate the volume to ⅒-1/50 of the original volume; then nanofiltration desalinated for 3~5 times when the buffer solution was added to dilute the volume to the original volume;
10) degerming and filteration, freeze-drying was carried out to prepare the bovine connective tissue protein peptide freeze-dried powder.

Example 3

Preparation of an Active Peptide Freeze-Dried Powder from Animal Cartilage

Human and vertebrate-specific embryonic bones. The material can be divided into transparent cartilage, elastic cartilage and fiber cartilage, which is a slightly elastic tough tissue, and it plays a role of supporting and protecting the mechanism of body. The bone consists of chondrocytes, fibers, and matrix. The matrix contains 70% moisture and the organic component is primarily a variety of proteins, such as cartilage mucin, collagen and chondroalbuminoid, etc. In fetal and young age, cartilage tissue is wildly distributed, while later is replaced gradually by bone tissue. Adult cartilage is present at the articular surface of the bone, rib cartilage, trachea, pinna, intervertebral disc, etc.

The pig rib cartilage was taken, and crushed, and the bone powder was prepared; 8 Kg of pig bone powder was taken, and 5~10 times of volume of 0.05 MNaCl~3 M NaCl phosphate buffer solution (pH6.0~8.0) or 5~10 times of volume of deionized water was added into the bone powder for grinding; filtered to remove residues, and collected supernatant to obtain a protein crude product; 3~5 weight volume of a phosphate buffer solution was added into the crude protein product, for stirring, pH was adjusted to 6.8~7.4, which contains 0.05 M~0.1 MNaCl; 1~4% of neutral protease was added, for enzymolysis; and filtered with 0.2 μm filter membrane; The crude filtrate was first filtered by a filter membrane with molecular weight cut-off between 6000-8000, passed liquid was collected, then when the phosphate buffer solution was added to the original volume, repeatedly filtered for 3~5 times, and the residue was preserved for later use; nanofiltration of the filtrate was carried out by a nanofiltration membrane with molecular weight cut-off between 300~800 to concentrate the filtrate to ⅕~1/50 of the original volume, then nanofiltration desalinated for 3~5 times when the buffer solution was added to dilute the volume to the original volume, degerming; ultra-low temperature vacuum freeze drying was carried out to prepare the porcine cartilage protein peptide freeze-dried powder.

Example 4

Preparation of an Active Peptide Freeze-Dried Powder from Animal Bone Marrow

The bone marrow was taken from the bone; 2 Kg of the bone marrow was taken, and 5~10 times of volume of 0.05 M NaCl~3 MNaCl phosphate buffer solution (pH 6.0~8.0) or 5~10 times of volume of deionized water was added into the bone marrow to homogenize; filtered to remove residues, and the supernatant was collected to obtain a protein crude product; 3~5 wt % of a phosphate buffer solution was added into the protein crude product, for stirring, pH was adjusted to 6.8~7.4, which contains 0.05 M~0.1 MNaCl; and 2~4.5% Serine protease was added into the protein crude product, for enzymolysis; The crude filtrate was firstly filtered by a filter membrane with molecular weight cut~off of 5000, filtrate was collected, then when the phosphate buffer solution was added to the original volume, repeatedly filtered for 3~5 times, and the residue was preserved for later use; nanofiltration of the filtrate was firstly carried out by a nanofiltration membrane with molecular weight cut-off of 400 to concentrate the filtrate to ⅒~1/50 of the original volume, then nanofilteration desalinated the buffer solution for 3~5 times when the buffer was added to dilute the volume to the original volume, degerming and filtration, and freeze-drying was carried out to prepare the cattle connective tissue protein peptide freeze-dried powder.

Example 5

Preparation of an Active Peptide Freeze-Dried Powder from Animal Tendons

The beef tendon was taken, and crushed to prepare the tendon powder; 2 Kg of the tendon powder was taken, and 5~10 times of volume of 0.05M NaCl~3 M NaCl phosphate buffer solution (pH6.0~8.0) or 5~10 times of volume of deionized water was added into the tendon powder to grind; filtered to remove residues, and the supernatant was collected to obtain a protein crude product; 3~5 wt % of phosphate buffer solution was added into the protein crude product, for stirring, pH was adjusted to 6.8~7.4, which contains 0.05 M~0.1 M NaCl; 2~5% compound protease was added into the protein crude product, for enzymolysis; and the protein peptide crude product was filtered by 0.2 μm filter membrane; the crude filtrate was firstly filtered by a filter membrane with a molecular weight cut-off of 6000, passed liquid was collected, then when the phosphate buffer solution was added to the original volume, repeatedly filtered for 3~5 times, and the residue was preserved for later use; nanofiltration of the filtrate was carried out by a nanofiltration membrane with molecular weight cut-off of 800 to concentrate the filtrate to $1/5$~$1/50$ of the original volume, then nanofiltration desalinated the buffer solution for 3~5 times when the buffer was added to dilute the volume to the original volume, degerming and filtration, and freeze-drying was carried out to prepare the cattle connective tissue protein peptide freeze-dried powder.

Example 6

Preparation of an Active Peptide Freeze-Dried Powder from Animal Panel Tendons

The bull paddywack was taken, and crushed to prepare tendon powder; 2 Kg of the tendon powder was taken, and 5~10 times of volume of 0.05 M NaCl~3 M NaCl phosphate buffer solution (pH6.0~8.0) or 5~10 times of volume of deionized water was added into the tendon powder to grind; filtered to remove residues, and the supernatant liquid was collected to obtain a protein crude product; 3~5 wt % of phosphate buffer solution was added into the protein crude product, for stirring, pH was adjusted to 6.8~7.4, 2~5% of compound protease was added, for enzymolysis; the protein crude product was filtered by 0.2 μm filter membrane; the crude filtrate was first filtered by a filter membrane with molecular weight cut-off of 6000; passed liquid was collected, then when the phosphate buffer solution was added to the original volume repeatedly filtered for 3~5 times, while the residue was preserved for later use; nanofiltration of the filtrate was carried out by a nanofiltration membrane with molecular weight cut-off of 400 to concentrate the filtrate to $1/5$~$1/50$ of the original volume, then nanofiltration desalinated the buffer solution for 3~5 times when the buffer solution was added to dilute the volume to the original volume; degerming and filtration and freeze-drying was carried out to prepare the bull paddywack protein peptide freeze-dried powder.

Example 7

Preparation of an Active Peptide Freeze-Dried Powder from Animal Skin

The donkey skin was taken, and crushed to prepare donkey skin powder; 2 Kg of the donkey skin powder was taken, and 5~10 times of volume of 0.05M NaCl~3 M NaCl phosphate buffer solution (pH6.0~8.0) or 5~10 times of volume of deionized water was added into the donkey skin powder to grind; filtered to remove residues, and the supernatant was collected to obtain a protein crude product; 3~5 wt % of phosphate buffer solution was added into the protein crude product, for stirring, pH was adjusted to 6.8~7.4, which contains 0.05 M~0.1 MNaCl; 1~4.5% alkaline protease was added, for enzymolysis; and the protein crude product was filtered by 0.2 μm filter membrane; the crude filtrate was first filtered by a filter membrane with molecular weight cut-off of 8000~10000, passed liquid was collected, then when the phosphate buffer solution was added to the original volume, repeatedly filtered for 3~5 times, and the residue was preserved for later use; nanofiltration of the filtrate was carried out by a nanofiltration membrane with molecular weight cut-off of 800 to concentrate the filtrate to $1/5$~$1/50$ of the original volume, then nanofiltration desalinated the buffer solution for 3~5 times when the buffer was added to dilute the volume to the original volume; degerming and filtration, and freeze-drying was carried out to prepare the donkey skin protein peptide freeze-dried powder.

Example 8

Preparation of an Active Peptide from Cowhide

Cowhide was taken; cut by machine, and chopped and mixed by chopper mixer; after chopped, 5~10 times of volume of buffer solution with pH 6.5~8.5 was added for stirring and washing; acid extraction; salting out; pulp grinding and/or homogenizing; The pH was adjusted to 6.5~8.5, pepsinolysis; rough filtrated; The filtrate was filtered by a filter membrane with molecular weight cut-off of 8000, passed liquid was collected, then when the phosphate buffer solution was added to the original volume, repeatedly filtered for 3~5 times, and the residue was preserved for later use; nanofiltration of the filtrate was carried out by a nanofiltration membrane with molecular weight cut-off of 300~800 to concentrate the filtrate to $1/5$~$1/50$ of the original volume, then nanofiltration desalinated the buffer solution for 3~5 times when the buffer was added to dilute the volume to the original volume; degerming; ultra-low-temperature vacuum freeze-drying was carried out to prepare the cowhide protein peptide freeze-dried powder.

Example 9

Preparation of an Active Peptide Freeze-Dried Powder from Animal Stomach

Animal stomach was taken, crushed to prepare gastric powder; 2 Kg of gastric powder was taken, 5~10 times of volume of 0.05 M NaCl~3 M NaCl phosphate buffer solution (pH 6.0~8.0) or 5~10 times of volume of deionized water was added into the gastric powder to grind; filtered to remove residues, and the supernatant was collected to obtain a protein crude product; 3~5 wt % of phosphate buffer solution was added into the protein crude product, for stirring, pH was adjusted to 6.8~7.4, which contains 0.05 M~0.1 NaCl; enzymolysis with pepsin; Coarse Filtration; the filtrate was filtered by a filter membrane with molecular weight cut-off of 6500, passed liquid was collected, then when the phosphate buffer solution was added to the original volume, repeatedly filtered for 3~5 times, and the residue was preserved for later use; nanofiltration of the filtrate was carried out by a nanofiltration membrane with molecular weight cut-off of 300-500 to concentrate the filtrate to $1/5$~$1/50$ of the original volume, then nanofiltration desalinated the buffer solution for 3~5 times when the buffer was added to dilute the volume to the original volume and sterilization; ultra-low-temperature vacuum freeze-drying to prepare the animal stomach protein peptide freeze-dried powder.

Example 10

Preparation of an Active Peptide Freeze-Dried Powder from Animal Intestine

Animal intestine was taken, crushed, to prepare intestinal powder; 2 Kg of intestinal powder was taken, 5~10 times of volume of 0.05 M NaCl~3 M NaCl phosphate buffer solution (pH6.0~8.0) or 5~10 times of volume of deionized water was added into the intestine powder to grind; filtered to remove residues, and the supernatant was collected to obtain a protein crude product; 3~5 wt % of a phosphate buffer solution was added into the protein crude product, for stirring, pH was adjusted to 6.8~7.4, which contains 0.05 M~0.1 MNaCl; the protein peptide course product was filtered with a 0.2 μm filter membrane; 1~3% papain and Bacillus subtilis and sulfhydryl protease were added for enzymolysis; and the protein crude product is filtered by 0.2 μm filter membrane; The crude filtrate was first filtered by a filter membrane with molecular weight cut-off of 8000~10000, passed liquid was collected, then when the phosphate buffer solution was added to the original volume, repeatedly filtered for 3~5 times, and the residue was preserved for later use; nanofiltration of the filtrate was carried out by a nanofiltration membrane with molecular weight cut-off of 800 to concentrate the filtrate to ⅕~1/50 of the original volume, then nanofilteration desalinated the buffer solution for 3~5 times when the buffer solution was added to dilute the volume to the original volume; sterilization and filtration, and freeze-drying was carried out to prepare the animal intestinal protein peptide freeze-dried powder.

Example 11

Preparation of an Active Peptide Freeze-Dried Powder from Omasum

Beef trip (omasum) was taken after slaughted, crushed, to prepared omasum powder; 5~10 times of volume of deionized water was added into omasum powder to grind; 10 Kg of the above omasum powder was taken, extracted by acetic acid with a final concentration of 0.05~25% for 4~24 hours, filtered to remove residues, the supernatant was collected to obtain a protein crude product, 3~5 wt % of a phosphate buffer solution was added into the protein crude product, for stirring, pH was adjusted to 6.8~7.4, which contains 0.05 M~0.1 M NaCl, 1~3% protease and chymosin compound were added for enzymolysis; and the protein peptide crude product was filtered by 0.2 μm filter membrane; The crude filtrate was first filtered by a filter membrane with molecular weight cut-off of 8000, filtrate was collected, then when the phosphate buffer solution was added to the original volume, repeatedly filtered for 3~5 times, and the residue was preserved for later use; nanofiltration of the filtrate was first carried out by a nanofiltration membrane with molecular weight cut-off of 750 to concentrate the filtrate to 1/10~1/50 of the original volume, then nanofiltration desalinated the buffer solution for 3~5 times when the buffer solution was added to dilute the volume to the original volume; sterilization and filtration and freeze-drying was carried out to prepare the omasum protein peptide freeze-dried powder.

Example 12

Preparation of an Active Peptide Freeze-Dried Powder from Animal Muscle

Animal muscle was taken and crushed, and slurry was prepared; 2 Kg of smooth muscle powder was taken, and 5~10 times of volume of 0.05 MNaCl~3 M NaCl phosphate buffer solution (pH6.0~8.0) or 5~10 times of volume of deionized water was added into the smooth muscle powder; the residue was removed by filtration, and the supernatant liquid was collected to obtain a protein crude product; 3~5 weight volume of phosphate buffer solution was added to the protein crude product, stirred, pH was adjusted to 6.8~7.4, which contains 0.05 M-0.1 M NaCl; 1~3% serine protease, neutral protease, pepsin and trypsin were added for enzymolysis; the protein peptide crude product was filtered with a 0.2 μm filter membrane; the crude filtrate first was filtered by a filter membrane with a molecular weight cut-off of 6000, filtrate was collected, then when the phosphate buffer solution was added to the original volume, repeatedly filtered for 3~5 times, while the residue was preserved for later use; nanofiltration was first carried out by nanofiltration membrane with molecular weight cut-off of 600 to concentrate the volume to 1/10~1/50 of the original volume, then nanofiltration desalinated the buffer solution for 3~5 times when the buffer solution was added to dilute the volume to the original volume; sterilization filtration and freeze-drying was carried out to prepare the meat protein peptide freeze-dried powder.

Example 13

Preparation of an Active Peptide Freeze-Dried Powder from Animal Intramuscular Connective Tissues Animal muscle was taken and crushed, and slurry was prepared; 2 Kg of the animal intramuscular connective tissue powder was taken, and 5~10 times of volume of 0.05 M NaCl~3 MNaCl phosphate buffer solution (pH6.0~8.0) or 5~10 times of volume of deionized water was added into the animal intramuscular connective tissue powder; filtered to remove residues, and the supernatant was collected to obtain a protein crude product; 1~3% of alkaline protease, serine protease, neutral protease, pepsin and trypsin enzyme were added for enzymolysis; and the protein peptide crude product was filtered by 0.2 μm filter membrane; The crude filtrate first was filtered by a filter membrane with a molecular weight cut-off of 6000, filtrate was collected, then when the phosphate buffer solution was added to the original volume, repeatedly filtered for 3~5 times, and the residues was preserved for later use; nanofiltration was first carried out by a nanofiltration membrane with molecular weight cut-off of 400 to concentrate the volume to 1/10~1/50 of the original volume, then nanofiltration desalinated the buffer solution for 3~5 times when the solution was added to dilute the volume to the original volume; sterilization and filtration and freeze-drying was carried out to prepare animal intramuscular connective tissue protein peptide freeze-dried powder.

Example 14

Preparation of an active Peptide Freeze-Dried Powder From Animal Interosseus Muscle Animal interosseus muscle was taken and crushed to prepare slurry; 2 Kg of the animal interosseus muscle powder was taken, and 5~10 times of volume of 0.05 M NaCl~3 MNaCl phosphate buffer solution (pH6.0~8.0) or 5~10 times of volume of deionized water was added into the animal interosseus muscle powder; filtered to remove residues, and the supernatant liquid was collected to obtain a protein crude product; 3~5 wt % of phosphate buffer solution was added into the crude protein product, stirred, pH was adjusted to 6.8~7.4, which contains 0.05M~0.1 M NaCl; 1~3% of neutral protease, compound protease and chymosin were added for enzymolysis; and the protein peptide crude product was filtered by 0.2 μm filter membrane; The crude filtrate first was filtered by a filter membrane with a molecular weight cut-off of 5000, filtrate was collected, then when the phosphate buffer solution was added to the original volume, repeatedly filtered for 3~5 times, and the residues was preserved for later use; nanofiltration was first carried out by a nanofiltration membrane with molecular weight cut-off of 600 to concentrate the volume to 1/10~1/50 of the original volume, then nanofiltration desalinated the buffer solution for 3~5 times when the solution was added to dilute the volume to the original volume; sterilization and filtration and freeze-drying was carried out to prepare the animal interosseus muscle protein peptide freeze-dried powder.

Example 15

Preparation of an Active Peptide Freeze-Dried Powder from Cartialgenous

Cartialgenous was taken; machine-broke to prepare powder; 5~10 times of volume of pH 6.5-8.5 buffer solution was added for stirring and washing; the pH was adjusted to 6.5-8.5, enzymolysis; coarse filtration; the filtrate was filtered by a filter membrane with molecular weight cut-off of 6000~8000, passed liquid was collected, then the phosphate buffer solution was added to the original volume, repeatedly filtered for 3~5 times, and the residue was preserved for later use; The filtrate was then filtered by a nanofiltration membrane with molecular weight cut-off of 300~800 to concentrate the volume to 1/5-1/50 of the original volume, then nanofiltration desalinated the buffer solution for 3~5 times when the solution was added to dilute the volume to the original volume; sterilization; and ultra-low temperature vacuum freeze-drying was carried out to prepare the cartialgenous protein peptide freeze-dried powder.

By comparison, the activity of the high-activity protein peptide produced by the process is obviously higher than foreign imported protein peptide commodities. This has a close relationship to the production process technology of the active protein peptide, while current commercialized active protein peptide tends to use strong acids, strong base preparation processes which essentially made most of the protein degenerated, and the natural structural conformation is lost, as well as their biological activity. The protein peptide produced by the process is extracted under the condition of low temperature (18° C.), in which the original three-dimensional conformation of the protein peptide is reserved to the greatest extent, so that the protein peptide has high biological activity, which play an important role in treatment of diseases of one or more of groups consisting of hypertension, hyperlipidemia, lipid deposition caused by metabolic disorders, obesity, arteriosclerosis, prostatitis, respiratory infectious diseases, senile dementia, diabetes, aging diseases, coronary heart disease, sexual dysfunction, chronic obstructive pulmonary emphysema, hepatitis, fatigue, neurasthenia, cerebral infarction, asthma, cough, arthritis, rheumatoid arthritis, multiple bone myeloma, disc injury, osteoporosis, cardiovascular disease, myocarditis, adult respiratory distress syndrome. Significant clinical effects have been highlighted. The present invention is not limited to the specific embodiment described in this application, and as a single description of the individual aspects of the invention. It will be understood by those skilled in the art that various modifications and changes may be made without departing from the spirit and scope of the present application. According to the above description, in addition to those enumerated herein, functionally equivalent uses within the scope of the present disclosure are apparent to those skilled in the art. Such alterations and modifications are intended to fall within the scope of the appended claims. The disclosure is limited only by the appended claims, along with the full scope of equivalents to which such claims are entitled. It should be understood that the present disclosure is not limited to particular methods, reagents, compositions, and biological systems, although, of course, the methods, reagents, compositions, and biological systems may vary. It is also to be understood that the terms used herein are for the purpose of describing particular embodiment only and is not used for limitation. All patents, patent applications, prior applications, and publications referred to or cited herein are incorporated by reference in their entirety so that they do not to contradict the clear instruction of description. Other embodiments are contemplated within the scope of the claims.

The invention claimed is:

1. A method for preparing an active protein peptide from an animal connective tissue, the method comprising:
   washing and shredding the animal connective tissue, thereby obtaining shredded connective tissues;
   extracting a crude protein product from the shredded connective tissues by adding a phosphate buffer solution, containing 0.05-3 M NaCl, of pH 6.0 to 8.0;
   pulp grinding and/or homogenizing the crude protein product to obtain a homogenized sample;
   adjusting a pH of the homogenized sample to 6.5-8.0 to obtain a connective tissue slurry;
   conducting an enzymolysis of the connective tissue slurry, thereby obtaining a protein peptide enzymolysate;
   carrying out filtration and nanofiltration of the protein peptide enzymolysate, thereby obtaining a filtrate;
   degerming the filtrate, thereby obtaining a degermed sample; and
   vacuum freeze-drying the degermed sample, thereby obtaining an active protein peptide.

2. The method according to claim 1, wherein the animal connective tissue is one or more connective tissues existing in spine, protuberance, horn, bone, cartilage, bone marrow, joint, membrane, ligament, tendon, tendon interval, sinew, tendon of beef and mutton, plate tendon, plate tendon tip, whole plate tendon, interrupted tendon, sinew tendon, spoon tendon, front tendon, rear tendon, tendon muscle, diaphragms, brisket tendon, sirloin tendon, strain tendon, smooth muscle, louver, or tripe.

3. The method according to claim 1, wherein the animal connective tissue is fresh, low temperature maintained, or frozen.

4. The method according to claim 3, wherein the animal connective tissue is fresh.

5. The method according to claim 1, wherein an enzyme used for the enzymolysis is one or more selected from the group consisting of serine protease, alkaline protease, sulfhydryl protease, neutral protease, bromelain, metalloproteinase, aspartic protease, carboxypeptidase, pepsin, chymotrypsin, trypsin, cathepsin K, chymotrypsin, flavor protease, compound protease, papain, and subtilisin.

6. The method according to claim 5, wherein the enzyme used for the enzymolysis is one or more selected from the group consisting of serine protease, alkaline protease, neutral protease, pepsin, trypsin, compound protease, and papain.

7. The method according to claim 5, wherein in the process of the enzymolysis, the connective tissue slurry is first adjusted the temperature to 0-65° C., and the enzymolysis time is 1-24 hours.

8. The method according to claim 7, wherein in the process of the enzymolysis, the connective tissue slurry is first adjusted the temperature to 30-45° C., and the enzymolysis time is 8-24 hours.

9. The method according to claim 1, wherein the carrying out the filtration and the nanofiltration comprises filtering the protein peptide enzymolysate by a filter membrane of 0.2-0.4 um, then filtering by a filter membrane with molecular weight cut-off between 4500 and 10000, finally filtering the filtrate by nanofiltration membrane with molecular weight cut-off between 250 and 800, to concentrate the volume to 1/5-=1/50 of original volume, then adding the buffer solution to dilute the filtrate to the original volume, and repeating the above process for 3-5 times.

10. The method according to claim 1, wherein the method does not extract the crude protein product using an acid.

* * * * *